(12) United States Patent
Liao

(10) Patent No.: US 7,840,053 B2
(45) Date of Patent: Nov. 23, 2010

(54) SYSTEM AND METHODS FOR TOMOGRAPHY IMAGE RECONSTRUCTION

(76) Inventor: Hstau Y. Liao, 1405 Como Ave., SE., Apt. 13, Minneapolis, MN (US) 55414

( * ) Notice: Subject to any disclaimer, the term of this patent is extended or adjusted under 35 U.S.C. 154(b) by 901 days.

(21) Appl. No.: 11/732,899

(22) Filed: Apr. 5, 2007

(65) Prior Publication Data
US 2008/0247502 A1 Oct. 9, 2008

(51) Int. Cl.
*G06K 9/00* (2006.01)
(52) U.S. Cl. ................................. 382/131; 378/4
(58) Field of Classification Search ............... 382/131; 378/4
See application file for complete search history.

(56) References Cited

U.S. PATENT DOCUMENTS

| | | | |
|---|---|---|---|
| 4,293,912 A | 10/1981 | Walters | |
| 4,888,693 A | 12/1989 | Tam | |
| 5,270,926 A | 12/1993 | Tam | |
| 5,278,884 A | 1/1994 | Eberhard et al. | |
| 5,341,460 A | 8/1994 | Tam | |
| 5,909,476 A | 6/1999 | Cheng et al. | |
| 5,995,580 A | 11/1999 | Schaller | |
| 6,151,377 A | 11/2000 | Nilsson | |
| 6,246,742 B1 | 6/2001 | Besson et al. | |
| 6,408,088 B1 | 6/2002 | Hu | |
| 6,549,606 B1 | 4/2003 | Vaillant et al. | |
| 6,577,700 B1 | 6/2003 | Fan et al. | |
| 6,751,284 B1 | 6/2004 | Claus et al. | |
| 6,768,782 B1 | 7/2004 | Hsieh et al. | |
| 6,907,102 B1 | 6/2005 | Sauer et al. | |
| 6,934,352 B2 | 8/2005 | Freytag et al. | |
| 6,983,182 B2 | 1/2006 | Mistretta | |
| 6,987,829 B2 | 1/2006 | Claus | |
| 7,034,303 B2 | 4/2006 | Schotland et al. | |
| 7,158,823 B2 | 1/2007 | Hawkins | |
| 2006/0146983 A1 | 7/2006 | Kalke et al. | |
| 2009/0185655 A1* | 7/2009 | Koken et al. | 378/11 |

FOREIGN PATENT DOCUMENTS

WO    WO 03/041583    5/2003

OTHER PUBLICATIONS

Bieberle et al., "Evaluation of a limited angle scanned electron beam x-ray CT approach for two-phase pipe flows", 2006, IOP, 2057-2065.*

Fu et al., "Optimized algebraic reconstruction technique for generation of grain maps based on three-dimensional x-ray diffraction (3DXRD)", Nov. 2006, SPIE, 1-9.*

(Continued)

*Primary Examiner*—Vikkram Bali
*Assistant Examiner*—Katrina Fujita
(74) *Attorney, Agent, or Firm*—Charles C. Valauskas; Allison M. Corder

(57) ABSTRACT

The present invention is a tomographic reconstruction algorithm, which is highly effective improving image quality and accuracy by reducing or eliminating artifacts within images produced by limited data tomography. Using algebraic reconstruction techniques (ART), depending on whether or not an object has higher or lower densities, a current threshold value is set to either a high or low threshold parameter and then decreased or increased, respectively, to reduce or eliminate the artifacts in a reconstructed image.

12 Claims, 3 Drawing Sheets

OTHER PUBLICATIONS

Liao et al., "A Gradually Unmasking Method for Limited Data Tomography", 2007, IEEE, 820-823.*

E. Candes, J. Romberg, and T. Tao. Robust uncertainty principles: exact signal reconstruction from highly incomplete frequency information. *IEEE Trans. Inform. Theory*, 52:489-509, 2006.

A.H. Delaney and Y. Bresler. Globally convergent edgepreserving regularized reconstruction: an application to limited-angle tomography. *IEEE. Trans. Imag. Proc.*, 7:204-221, 1998.

G.T. Herman. *Image Reconstruction from Projections: The Fundamentals of Computerized Tomography*. Academic Press, New York, 180-205, 1980.

G.T. Herman and A. Lent. A computer implementation of a Bayesian analysis of image reconstruction. *Inform. and Control*, 31:364-384, 1976.

J.A. Högbom. Aperture synthesis with a non-regular distribution of interferometric baselines. *Astron. Astrophys. Supp.*, 15:417-426, 1974.

F. Natterer and F. Wuebbeling. *Mathematical Methods in Image Reconstructions*. SIAM, Philadelphia, 110-119, 2001.

M. Persson, Bone T., and H. Elmqvist. Total variation norm for three-dimensional iterative reconstruction in limited view angle tomography. *Phys. Med. Biol.*, 46:853-866, 2001.

M. Rantala, S. Vanska, Järvenpää S., Kalke M., Lassas M., Moberg J., and S. Siltanen. Wavelet-based reconstruction for limited angle X-ray tomography. *IEEE Trans. Med. Imag.*, 25:210-217, 2006.

L. Rudin, S. Osher, and E. Fatemi. Nonlinear total variation based noise removal algorithms. *Physica D*, 60:259-268, 1992.

S.H.W. Scheres, R. Marabini, S. Lanzavecchia, F. Cantele, Rutten T., S.D. Fuller, J.M. Carazo, R.M. Burnett, and C. San Martin. Classification of single projection reconstructions for cryo-electron microscopy data of icosahedral viruses. *J. Struct. Biol.*, 151:79-91, 2005.

* cited by examiner

SYSTEM AND METHODS FOR TOMOGRAPHY IMAGE RECONSTRUCTION

FIELD OF THE INVENTION

The present invention relates to tomography. More particularly, the present invention is directed to a system and methods for tomography image reconstruction using an algorithm to improve image quality and accuracy by reducing or eliminating artifacts.

BACKGROUND OF THE INVENTION

Tomography is used in medicine, archaeology, biology, geophysics, materials science, electron microscopy, security scanning, industrial nondestructive testing, astronomy and others. Tomography is imaging by sections or sectioning to convey internal structures of a solid object, for example the human body or the earth. Slices of the object are viewed without physically cutting the object. A device used in tomography is called a tomograph. A tomograph generates a tomogram, or image.

The image, or tomogram, can be achieved by tomography applications such as atom probe tomography (APT), computed tomography (CT), confocal laser scanning microscopy (LSCM), cryo-electron tomography (Cryo-ET), electrical capacitance tomography (ECT), electrical resistance tomography (ERT), electrical impedance tomography (EIT), functional magnetic resonance imaging (fMRI), magnetic induction tomography (MIT), magnetic resonance imaging (MRI), formerly known as magnetic resonance tomography (MRT), neutron tomography, optical coherence tomography (OCT), optical projection tomography (OPT), process tomography (PT), positron emission tomography (PET), quantum tomography, single photon emission computed tomography (SPECT), seismic tomography, and X-ray tomography.

In each tomography application, a source emits beams onto or from the object, which are then collected by a detector system. Beams include X-rays, gamma rays, positron electron annihilation reaction, radio frequency, nuclear magnetic resonance, ultrasound, electrons, ions, electron beams, radio pharmaceuticals, light, microwaves, magnetic field, to name a few. Beams are emitted with a scanning geometry such as parallel beams and circular trajectory beams, divergent beams (fan or cone) and circular trajectory beams, cone beams and helical trajectory beams, for example.

For example, in a transmission computed tomography system, a source projects a beam with scanning geometry that passes through the object, and transmits upon an array of detectors. The intensity of the transmitted radiation is dependent upon the attenuation of the object. As another example, in some emission computed tomography systems, the distribution of radio-isotopes within an object is transmitted upon an array of detectors. The detectors produce projection data, which is a separate electrical signal resultant from scanning geometry.

The projection data is then sent to a computer for processing to generate a two-dimensional or three-dimensional image, or reconstructed image. In most cases the computer processes the data based on the mathematical procedure called tomographic reconstruction. Tomographic reconstruction includes algorithms that manipulate the projection data to produce the image.

Many different reconstruction algorithms exist. Most algorithms fall into one of two categories: filtered back projection (FBP) and iterative reconstruction (IR). Usually, these algorithms provide inexact results: they represent a compromise between accuracy and computational time required. FBP demands fewer computational resources, while IR generally produces fewer artifacts. Artifacts are errors resultant from the reconstruction. FBP includes analytical methods, such as those that involve Fourier transform. IR includes algebraic methods and probabilistic methods.

Analytical methods are the fastest with respect to computational time required, whereas probabilistic methods are slower but provide more accurate results. Algebraic methods provide a relatively fast computational time along with accurate results.

Ideally, projection data should be collected as finely sampled as possible and covering a full angular range. The full angular range can be, for example, 180 degrees or 360 degrees. Projection data is a collection of one or more projections. A projection is commonly referred to the data collected in one angle. In practice it is very often that projection data are sparsely sampled or limited to a certain angular range. Limited data tomography refers to either (1) that the projection data is acquired within a limited (i.e., less than the full) angular range ("limited angle data") or (2) that a few number of projections are acquired ("sparse projection data").

Algorithms used in limited data tomography results in errors, or artifacts within the reconstructed image. Limited angle data tomography typically causes "fan-shape" or "butterfly" artifacts within the reconstructed image. Sparse projection data tomography typically causes "star-pattern" artifacts within the reconstructed image.

In dealing with the limited data tomography, many algorithms have been proposed such as Fourier methods, sinogram methods, regularization methods, Bayesian method, wavelet techniques, etc. Most of these algorithms are vulnerable to artifacts, unless a "reference image" is used, which is not always available.

There is a desire to provide an algorithm that improves quality and accuracy within a reconstructed image by reducing or eliminating artifacts. There is also a desire to provide an algorithm that can be applied to many tomography applications.

SUMMARY OF THE INVENTION

The present invention is a system and methods tomographic reconstruction algorithm applied in limited data tomography applications. The tomographic reconstruction algorithm of the present invention improves image quality and accuracy by reducing or eliminating artifacts within images.

The algorithm of the present invention is based on the algebraic reconstruction techniques (ART) of iterative reconstruction (IR). The present invention gradually recovers (or "unmasks") the densities, or reconstructive values, in the image. For example, in some transmission computed tomography systems, the density is related to the attenuation; whereas in some emission computed tomography system, the density is related to the distribution of the radio-isotopes inside the object.

An object of the present invention is to provide an algorithm that can be used with any algebraic reconstruction technique (ART). The present invention applies a "trick" to the ART algorithm, or transformation, that aims at reducing or eliminating artifacts. The "trick" is applied between two iterative steps of the ART algorithm and transforms the image by reducing or eliminating artifacts. Interleaved with the iterative steps, the reconstructed values are then set to be greater than or equal to a threshold t, which in turn is slowly decreased during the run. Thus, the threshold t is initially set to a high threshold parameter a and then decreased to a low threshold parameter b. This strategy applies, in general to images with higher densities than the surrounding medium. If instead the object has lower densities than the surrounding medium, in general, the reconstructed values are set to be smaller than or equal to a threshold t, which is slowly increased during the run. Thus, the threshold t is initially set to a low threshold parameter b and then increased to a high threshold parameter a.

For example, in the 2D case, with algebraic reconstruction techniques, the image solution C(x, y) is approximated by a weighted sum of basis functions, each of which is a shifted basic basis function b(x, y):

$$C(x, y) = \sum_{i,k} c_{ik} b(x - x_i, y - y_k). \quad (1)$$

The most common basic basis function is a pixel that has a square support and is valued one inside the support and zero otherwise, but it can be any basic basis function. The weights cik of the summation are the coefficients of the resulting approximated image vector.

In real applications, only a finite number of line integrals are measured indirectly. Let wl be a measured integrals along a line l, then for an image in the form (1) and in the absence of noise $$w_l = \sum_{i,k} c_{ik} r_{ik}(l), \quad (2)$$

where rik(l) is the integral of b (x−xi, y−yk) along l, which can be calculated from the scanning geometry of projection data collection. When noise is present, as it is the case in real applications, the equality in (2) becomes an approximation. In ART, a system of equalities, each of which in the form (2) is formed by considering all the lines along which data have been collected. An ART-type algorithm is essentially based on the following relaxation method for solving a consistent system of linear equalities. Let the system be $$Rc = w \quad (3)$$

with S unknowns and K equations. Equivalently, it can be written as a block system $$\begin{pmatrix} R_1 \\ \vdots \\ R_J \end{pmatrix} c = \begin{pmatrix} w_1 \\ \vdots \\ w_J \end{pmatrix}. \quad (4)$$

A relaxation method computes, in each iteration, $c^{(m,j)}$, for $1 \leq j \leq J$ and m=m=1, 2, ..., according to $$c^{(m,j)} = c^{(m,j-1)} + \lambda R_j^t A_j^{-1}(w_j - R_j c^{(m,j-1)}), \quad (5)$$

where $\lambda$ is a relaxation parameter, $A_j$ is a positive definite matrix of the appropriate size, $c^{(m,0)} = c^m$, and $c^{m+1} = c^{(m,J)}$. If $c^1$ is the S-dimensional vector of zeros, the sequence cm converges to the unique minimum Euclidean norm solution of the system (3).

In the inconsistent case, there is no convergence proof. However, ART-type algorithms are widespread, due to its relatively superior performance for various reconstruction tasks. In practice $\lambda$ is kept low, although any value is contemplated that reduces noise and/or that improves convergence speed. Another important parameter is the order in which the data is accessed. It has been observed that faster convergence can be achieved if a linear (i.e., increasing or decreasing) order is given up in favor of a non-sequential (e.g., directions that are as orthogonal as possible to the previous ones) order.

Another reason for its popularity is the possibility of incorporating prior knowledge in the reconstruction process. For example, if the image is known to be non-negative, then after each iteration the negative values can be set to zero prior to the next iterative step. Such adjustment has been shown to improve the speed of convergence to a desirable reconstruction. The application of a transformation of the image in between two iterative steps has been referred to as "trick". To be mathematically precise, in an ART-type algorithm with a "trick", the step in (5) is replaced by $$q = c^{(m,j-1)} + \lambda R_j^t A_j^{-1}(w_j - R_j c^{(m,j-1)}), \quad (6)$$

$$c^{(m,j)} = T_{m,j}(q), \quad (7)$$

where q is the intermediate image and $T_{m,j}$ is the transformation that defines the "trick".

In the case when the image consists of higher densities than the surrounding medium, the function $T_{m,j}(q)$ is generally set to be the following function of m and j $$T_{m,j}(q) = \max\{q, t_{m,j}\} \quad (8)$$

where $t_{m,j}$ is a threshold that decreases with m (and perhaps j as well). If instead the object has lower densities than the surrounding medium, then $T_{m,j}(q) = \min\{q, t_{m,j}\}$, and $t_{m,j}$ is increased. Consider, for example, $t_{m,j}$ to be linear in m and independent of j: $t_{m,j} = t_m = a - dm$, where a is the starting threshold and d>0 the "unmasking rate," which determines how fast the threshold is decreased.

Another object of the present invention is to significantly reduce or eliminate the artifacts in a reconstructed image. This enables, for example, an accurate recovery of the 3D structure of biological macromolecules that has impact on fields such as drug discovery. The present invention enables an increased accuracy in the detection of tumors/lesions. Likewise, the present invention can be used in dental applications, such as a root canal.

Yet another object of the present invention is to provide a method with easy implementation in many other tomography applications, including positron emission tomography (PET), single photon emission computed tomography (SPECT) and X-ray tomography.

Another object of the present invention is to provide a method that can be utilized with all scanning geometry, including parallel or divergent beams with circular or helical source trajectory, to name a few.

Another object of the present invention is to improve scanning efficiency and reduce cost by using fewer projections. The present invention eliminates the need for a favorable initial image that often influences the image during reconstruction. The present invention does not need a "reference image."

Another object of the present invention is to reduce radiation dosage.

Another object of the present invention is to provide robustness to noise. Noise is a disturbance that interferes with or prevents reception of a signal by the detector, thus noisy projection data results. The present invention provides an effective approach to noisy data, while improving quality and accuracy of the image with respect to contrast and shape.

Another object of the present invention is to eliminate requirement of a piecewise smoothness and a sharp boundary assumption.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to limit the invention, where like designations denote like elements, and in which.

DETAILED DESCRIPTION OF EMBODIMENTS OF THE INVENTION

Although the present invention is discussed in reference to 2D images, it is equally applicable to reconstructing 3D images. The present invention is discussed below with respect to a selected algebraic reconstruction technique (ART), but it is contemplated the present invention can be utilized with any ART algorithm.

Figure 1:
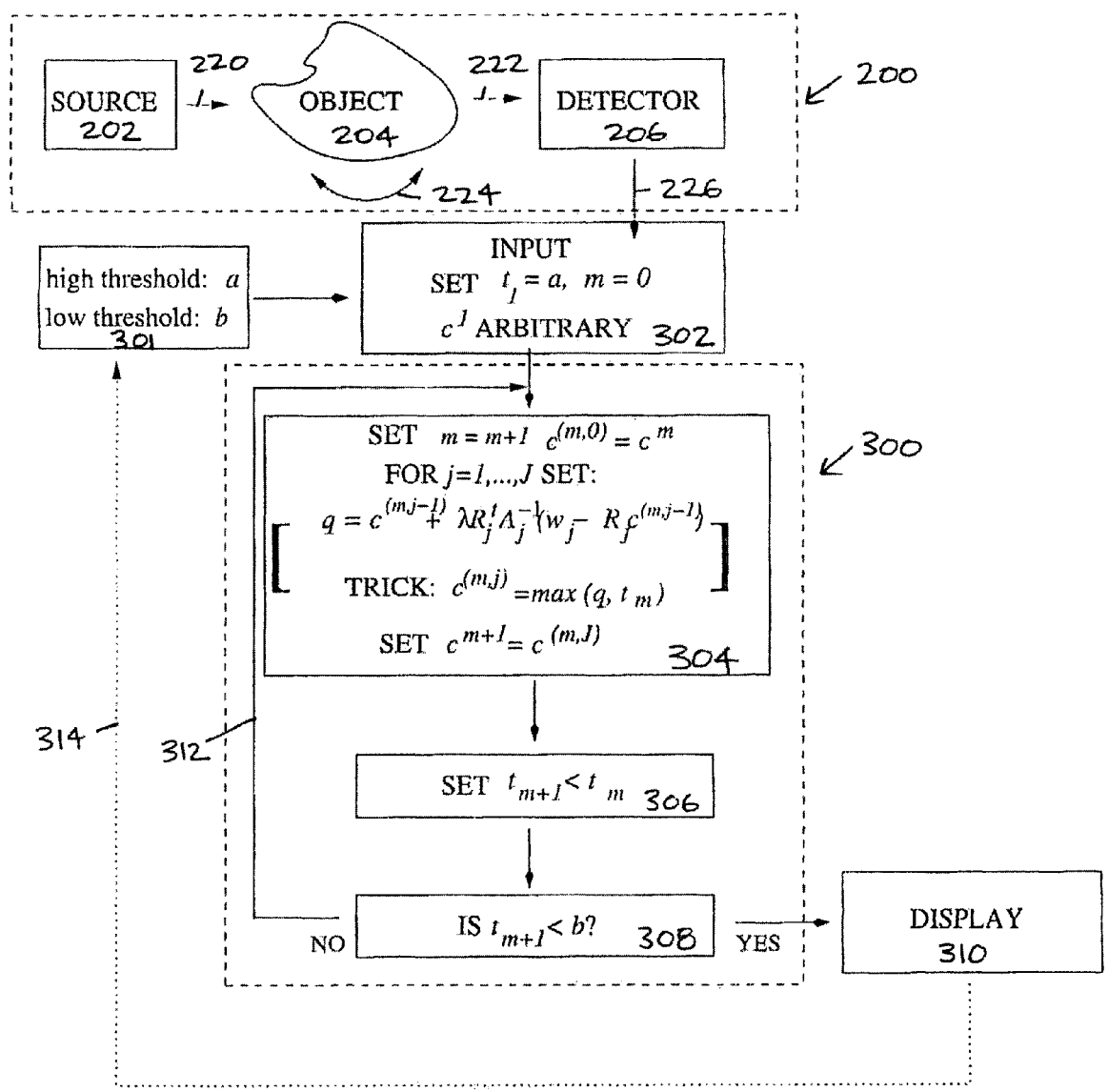
FIG. 1 illustrates a flow chart of a system and method of the algorithm according to the present invention.

FIG. 1 illustrates a flow chart of a system and method of a transmission computed tomography algorithm according to the present invention. If the object has higher densities than the surrounding medium, in general the reconstructed values are set to be greater than or equal to a current threshold t, which is slowly decreased during the run.

A tomograph 200 includes a source 202, object 204 and detector 206. Source 202 emits one or more beams 220 toward the object 204, which can rotate 224 with respect to the direction of the beams 220. Beams include, for example, X-rays, electrons, neutrons, microwaves.

The beams 220 emitted toward the object 204 include scanning geometry. The beams 220 are passed through the object 204, which are then projected by the object 204 in the form of attenuated radiation 222. The attenuated radiation 222 is transmitted upon an array of detectors 206. The attenuated radiation 222 arrives at the detectors 206, creating projection data 226. The projection data 226 is subject to the reconstruction algorithm 300 within a computer system. The system includes a display and a computer processor with a plurality of components.

The reconstruction algorithm 300 is an algebraic reconstruction technique (ART) with a "trick". Although the present invention is discussed below with respect to a particular ART algorithm, there are numerous ART algorithms to which the present invention is applicable. Along with the ART algorithm, the present invention uses a "trick" that reduces or eliminates artifacts.

As mentioned above, FIG. 1 is described in reference to objects with higher densities than the surrounding medium. As shown in FIG. 1, threshold parameters at step 301 are established. The current threshold value t is initially set to a high threshold parameter a at step 302. The projection data 226 is then subject to the reconstruction algorithm 300. The "trick" 304 is applied right after an iterative step of the ART algorithm 304. After applying one iterative step of the ART algorithm 304, reconstructive values are obtained. If the reconstructive values of the ART algorithm 304 are less than the current threshold value t, the reconstructive values are changed to equal the current threshold value t. The current threshold value t is slightly decreased at step 306 toward a low threshold parameter b. Step 308 is a termination test. If the current threshold value t is not lower than the low threshold parameter b as defined at step 301, the steps 304 through 308 repeat as shown by 312. Once the current threshold value t reaches below the threshold parameter b, the algorithm 300 stops and outputs the resulting image on display 310. Optionally, as shown by 314, the reconstructive values of the resulting image can be used to establish new threshold parameters of step 301.

Figure 2:
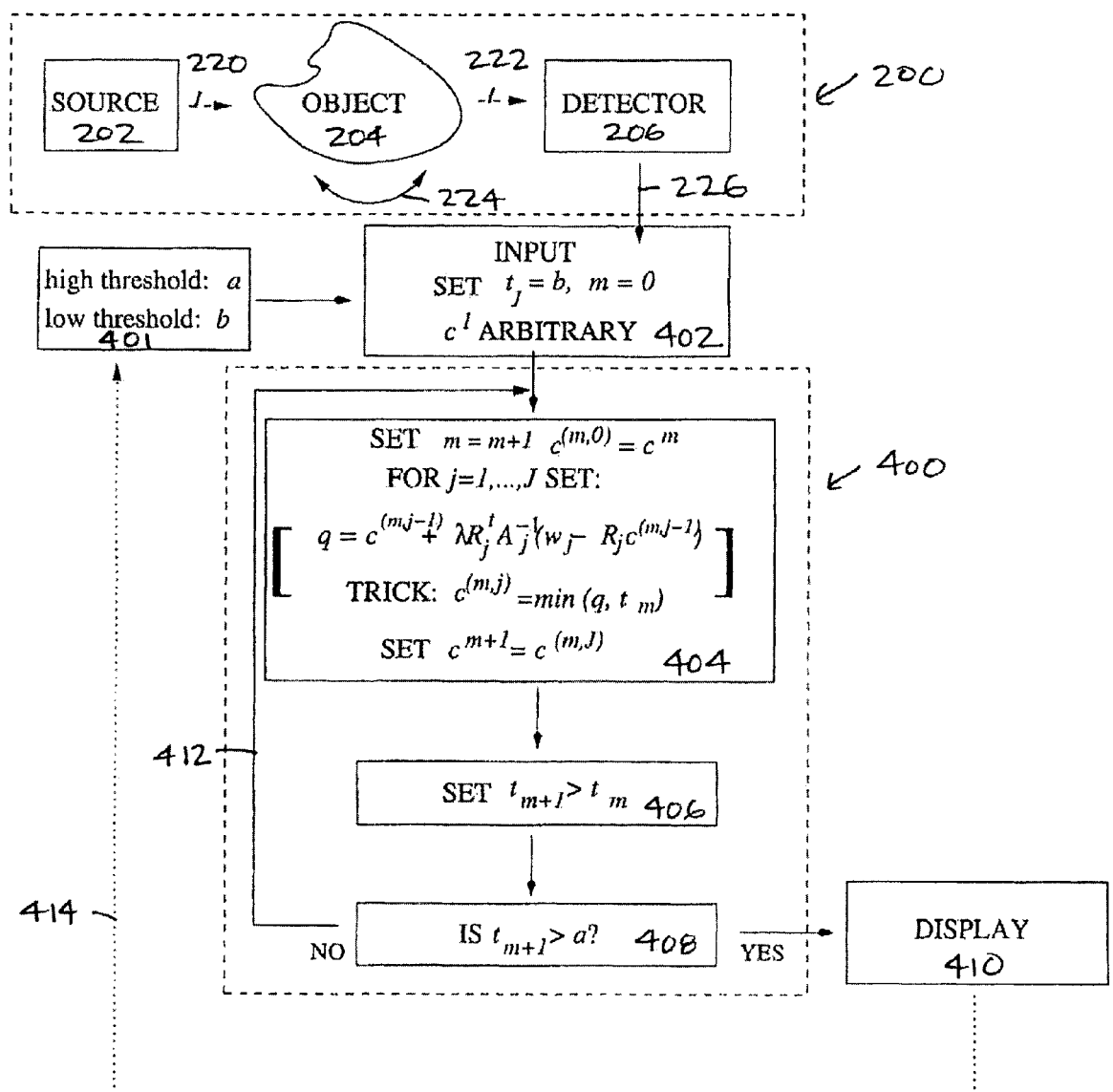
FIG. 2 illustrates a flow chart of another embodiment of a system and method of the algorithm according to the present invention.

FIG. 2 illustrates a flow chart of a system and method of a transmission computed tomography algorithm according to the present invention. If the object has lower densities than the surrounding medium, in general the reconstructed values are set to be smaller than or equal to a current threshold t, which is slowly increased during the run.

FIG. 2 is described in reference to images with lower densities than the surrounding medium. As shown in FIG. 2, threshold parameters at step 401 are established. The current threshold value t is initially set to a low threshold parameter b at step 402. The projection data 226 is then subject to the reconstruction algorithm 400. The "trick" 404 is applied right after an iterative step of the ART algorithm 404. After applying one iterative step of the ART algorithm 404, reconstructive values are obtained. If the reconstructive values of the ART algorithm 404 are greater than the current threshold value t, the reconstructive values are changed to equal the current threshold value t. The current threshold value t is slightly increased at step 406 toward a high threshold parameter a. Step 408 is a termination test. If the current threshold value t is not higher than the high threshold parameter a as defined at step 401, the steps 404 through 408 repeat as shown by 412. Once the current threshold value t reaches above the high threshold parameter a, the algorithm 400 stops and outputs the resulting image on display 410. Optionally, as shown by 414, the reconstructive values of the resulting image can be used to establish new threshold parameters of step 401.

Figure 3:
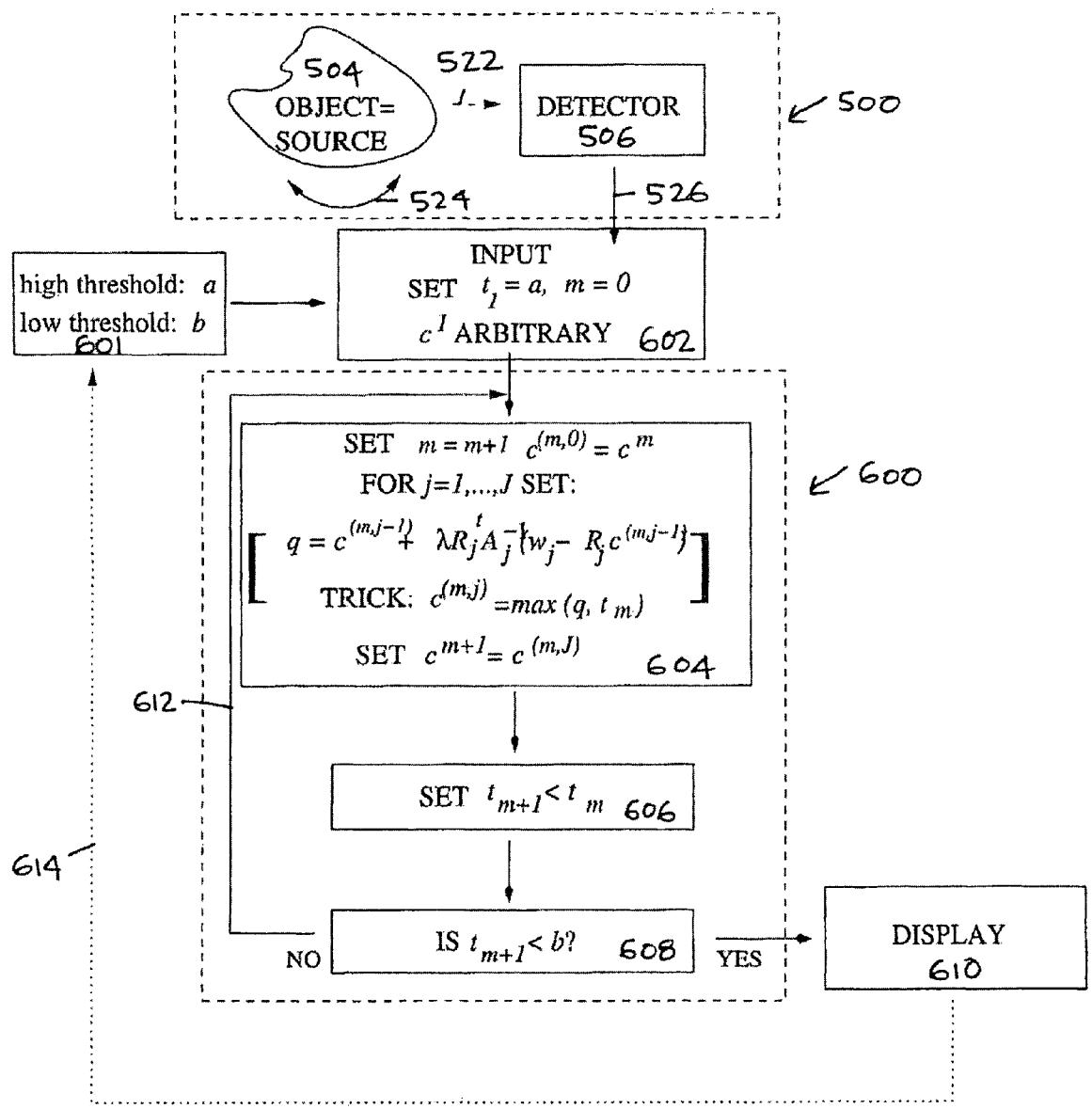
FIG. 3 illustrates a flow chart of another embodiment of a system and method of the algorithm according to the present invention.

FIG. 3 illustrates a flow chart of a system and method of an emission computed tomography algorithm according to the present invention. Emission computed tomography has a different arrangement of source-object-detector. Again, if the object has higher densities than the surrounding medium, in general the reconstructed values are set to be greater than or equal to a current threshold t, which is slowly decreased during the run, as shown in FIG. 3. If the object has lower densities than the surrounding medium, the reconstructed values are set to be smaller than or equal to a current threshold t, which is slowly increased during the run (not shown, but see FIG. 2).

A tomograph 500 includes a source/object 504 and detector 506. Source/object 504, which can rotate 524, emits beams 522, for example gamma rays, from inside the source/object 504.

The beams 522 are transmitted upon an array of detectors 506. The beams 522 arrive at the detectors 506, creating projection data 526. The projection data 526 is subject to the reconstruction algorithm 600 within a computer system. Again, the system includes a display and a computer processor with a plurality of components.

As shown in FIG. 5, threshold parameters at step 601 are established. The current threshold value t is initially set to a high threshold parameter a at step 602. The projection data 526 is then subject to the reconstruction algorithm 600. The "trick" 604 is applied right after an iterative step of the ART algorithm 604. After applying one iterative step of the ART algorithm 604, reconstructive values are obtained. If the reconstructive values of the ART algorithm 604 are less than the current threshold value t, the reconstructive values are changed to equal the current threshold value t. The current threshold value t is then slightly decreased at step 606 toward a low threshold parameter b. Step 608 is a termination test. If the current threshold value t is not lower than the threshold parameter b as defined at step 601, the steps 604 through 608 repeat as shown by 612. Once the current threshold value t reaches below the threshold parameter b, the algorithm 600 stops and outputs the resulting image on display 610. Optionally, as shown by 614, the reconstructive values of the resulting image can be used to establish new threshold parameters of step 601.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A method to reduce artifacts in limited data tomography, comprising:
    (a) providing an algebraic reconstruction technique algorithm including at least two iterative steps;
    (b) establishing a high threshold parameter and a low threshold parameter;
    (c) setting a current threshold value of a transformation equal to the high threshold parameter;
    (d) applying one iterative step of the algebraic reconstruction technique algorithm resulting in reconstructive values;
    (e) determining if the reconstructive values of the algebraic reconstruction technique algorithm are less than the current threshold value of the transformation;
    (f) changing the reconstructive values to equal the current threshold value of the transformation;
    (g) decreasing the current threshold value of the transformation slightly toward the low threshold parameter;
    (h) repeating the steps (d) through (g) until the current threshold value of the transformation reaches below the low threshold parameter; and
    (i) displaying the reconstructive values as an image.

2. The method of claim 1, further comprising the step (j) using the reconstructive values to establish the high threshold parameter and the low threshold parameter.

3. The method of claim 2, further comprising the step (k) rerunning the steps (c) through (i).

4. A method to reduce artifacts in limited data tomography, comprising:
    (a) providing an algebraic reconstruction technique algorithm including at least two iterative steps;
    (b) establishing a high threshold parameter and a low threshold parameter;
    (c) setting a current threshold value of a transformation equal to the low threshold parameter;
    (d) applying one iterative step of the algebraic reconstruction technique algorithm resulting in reconstructive values;
    (e) determining if the reconstructive values of the algebraic reconstruction technique algorithm are greater than the current threshold value of the transformation;
    (f) changing the reconstructive values to equal the current threshold value of the transformation;
    (g) increasing the current threshold value of the transformation slightly toward the high threshold parameter;
    (h) repeating the steps (d) through (g) until the current threshold value of the transformation reaches above the high threshold parameter; and
    (i) displaying the reconstructive values as an image.

5. The method of claim 4, further comprising the step (j) using the reconstructive values to establish the high threshold parameter and the low threshold parameter.

6. The method of claim 5, further comprising the step (k) rerunning the steps (c) through (i).

7. A system to reduce artifacts in limited data tomography, comprising:
    a computer including a computer processor with a plurality of components, wherein said computer processor includes an algebraic reconstruction technique algorithm including at least two iterative steps;
    a first computer processor component to establish a high threshold parameter and a low threshold parameter, wherein said first computer processor component sets a current threshold value of a transformation equal to said high threshold parameter;
    a second computer processor component to apply one iterative step of said algebraic reconstruction technique algorithm resulting in reconstructive values, wherein said second computer processor component determines if said reconstructive values of said algebraic reconstruction technique algorithm are less than said current threshold value of said transformation;
    a third computer processor component to change said reconstructive values to equal said current threshold value of said transformation, wherein said third computer processor component decreases said current threshold value of said transformation toward said low threshold parameter;
    a fourth computer processor component to monitor said transformation until said current threshold value of said transformation reaches below the low threshold parameter; and
    a display to illustrate said reconstructive values as an image.

8. The system of claim 7, wherein said reconstructive values establish said high threshold parameter and said low threshold parameter.

9. The system of claim 8, wherein said computer processor repeats said transformation.

10. A system to reduce artifacts in limited data tomography, comprising:
    a computer including a computer processor with a plurality of components, wherein said computer processor includes an algebraic reconstruction technique algorithm including at least two iterative steps;
    a first computer processor component to establish a high threshold parameter and a low threshold parameter, wherein said first computer processor component sets a current threshold value of a transformation equal to said low threshold parameter;
    a second computer processor component to apply one iterative step of said algebraic reconstruction technique algorithm resulting in reconstructive values, wherein said second computer processor component determines if said reconstructive values of said algebraic reconstruction technique algorithm are greater than said current threshold value of said transformation;

a third computer processor component to change said reconstructive values to equal said current threshold value of said transformation, wherein said third computer processor component increases said current threshold value of said transformation toward said high threshold parameter;

a fourth computer processor component to monitor said transformation until said current threshold value of said transformation above said high threshold parameter; and a display to illustrate said reconstructive values as an image.

11. The system of claim 10, wherein said reconstructive values establish said high threshold parameter and said low threshold parameter.

12. The system of claim 11, wherein said computer processor repeats said transformation.

* * * * *